United States Patent
Zhang et al.

(10) Patent No.: US 11,384,349 B2
(45) Date of Patent: Jul. 12, 2022

(54) **RECOMBINANT *BACILLUS SUBTILIS* ENGINEERED BACTERIUM CAPABLE OF EFFICIENTLY EXPRESSING KERATINASE**

(71) Applicant: Jiangnan University, Wuxi (CN)

(72) Inventors: Juan Zhang, Wuxi (CN); Zheng Peng, Wuxi (CN); Jian Chen, Wuxi (CN); Guocheng Du, Wuxi (CN); Xinzhe Mao, Wuxi (CN); Hengrui Zhou, Wuxi (CN)

(73) Assignee: Jiangnan University, Wuxi (CN)

( * ) Notice: Subject to any disclaimer, the term of this patent is extended or adjusted under 35 U.S.C. 154(b) by 0 days.

(21) Appl. No.: 17/104,122

(22) Filed: Nov. 25, 2020

(65) Prior Publication Data

US 2021/0079371 A1 Mar. 18, 2021

Related U.S. Application Data

(63) Continuation of application No. PCT/CN2018/089937, filed on Jun. 5, 2018.

(30) Foreign Application Priority Data

May 30, 2018 (CN) .......................... 2018105378113

(51) Int. Cl.
*C12N 9/54* (2006.01)
*C12N 1/20* (2006.01)
*C12R 1/125* (2006.01)

(52) U.S. Cl.
CPC .............. *C12N 9/54* (2013.01); *C12N 1/20* (2013.01); *C12N 1/205* (2021.05); *C12R 2001/125* (2021.05)

(58) Field of Classification Search
None
See application file for complete search history.

(56) References Cited

U.S. PATENT DOCUMENTS

| 2016/0058016 A1* | 3/2016 | Villegas Escobar ..... C12N 3/00 504/117 |
| 2019/0241924 A1* | 8/2019 | Tsukagoshi ............. C12P 21/00 |
| 2021/0079371 A1* | 3/2021 | Zhang ..................... C12N 1/20 |

FOREIGN PATENT DOCUMENTS

CN 106222190 A 12/2016

OTHER PUBLICATIONS

Machine English Translation of CN106222190A, Abstract, Specification and Claims, published Dec. 14, 2016 (Year: 2016).*

(Continued)

*Primary Examiner* — Richard C Ekstrom
(74) *Attorney, Agent, or Firm* — IPro, PLLC (57) ABSTRACT

The disclosure discloses a recombinant *Bacillus subtilis* engineered bacterium capable of efficiently expressing keratinase, and belongs to the technical fields of genetic engineering and fermentation engineering. The disclosure successfully constructs a genetically engineered bacterium *B. subtilis* WB600-pP43NMK-ker capable of efficiently expressing keratinase by using a keratinase gene from *Bacillus licheniformis* (BBE11-1) as a target gene, pP43NMK as an expression vector and *B. subtilis* WB600 as an expression host; and meanwhile, the disclosure conducts in-depth research on fermentation media and fermentation conditions when the engineered bacteria are configured as a production strain to produce keratinase to obtain a fermentation medium capable of increasing a yield of keratinase and an optimum process for fermentation production of keratinase.

4 Claims, 4 Drawing Sheets

Specification includes a Sequence Listing.

(56) References Cited

OTHER PUBLICATIONS

Liu. Bohong. Over Expression of Bacillus Licheniformis Keratinase, its Molecular Modification for Enhanced Thermostability and Substrate Specificity. China Doctoral Dissertations Full-text Database, Basic Sciences, No. No. 3, Mar. 15, 2015.
Yang, Sen et al. "Characterization and Application of Endogenous Phase-Dependent Promoters in Bacillus Subtilis" Appl Microbiol Biotechnol., vol. 101, No (10), Feb. 14, 2017 (Feb. 14, 2017).

* cited by examiner

RECOMBINANT *BACILLUS SUBTILIS* ENGINEERED BACTERIUM CAPABLE OF EFFICIENTLY EXPRESSING KERATINASE

TECHNICAL FIELD

The disclosure relates to a recombinant *Bacillus subtilis* engineered bacterium capable of efficiently expressing keratinase, and belongs to the technical fields of genetic engineering and fermentation engineering.

BACKGROUND

Keratinase is a specific protease capable of degrading an insoluble hard protein-keratin type substrate (such as feather, wool, hair and scurf), and it is mainly acquired when bacteria, fungi, actinomycetes and other microorganisms treat keratin as a monotonous carbon and nitrogen source for growth and secretion.

As a protease with wide substrate specificity and high hydrolytic catalysis capacity, the keratinase can replace traditional proteases to be widely applied to fields of feather degradation, leather textiles, feed additives, organic fertilizers, detergents and the like and has a huge market.

However, wild keratinase is far from meeting market demands due to its poor performance and low yield, and thus it is hard to be truly applied to industrial production.

Nowadays, a means of genetically engineered bacteria is often applied to reinforcing transcription and translation of a keratinase gene and realize the aims of efficiently expressing and actively secreting keratinase in bacteria, thereby effectively improving performance and yield of the keratinase. However, a genetically engineered bacterium capable of efficiently expressing keratinase is still unable to be successfully constructed at the present stage.

At present, heterologous expression hosts of the keratinase mainly include three types of bacteria: *Escherichia coli*, *B. subtilis* and *Pichia pastoris*. The *E. coli* has a clear genetic background and simple expression operation, but when a T7 strong promoter is adopted, an *E. coli* expression system easily forms inclusion bodies, which results in a low yield of keratinase; the *P. pastoris* hinders efficient production of keratinase due to its long fermentation cycle and other factors such as codon usage bias and enzyme molecule glycosylation; and the *B. subtilis* successfully expresses keratinase, but the keratinase is extremely low in yield and almost has no activity.

Therefore, it is urgent to construct a genetically engineered bacterium capable of efficiently expressing keratinase to meet market demands.

SUMMARY

The disclosure constructs a genetically engineered bacterium *B. subtilis* WB600-pP43NMK-ker capable of efficiently expressing keratinase by using a keratinase gene from a food safety strain *Bacillus licheniformis* (BBE11-1) as a target gene, pP43NMK as an expression vector and *B. subtilis* WB600 as an expression host; and meanwhile, the disclosure conducts in-depth research on fermentation media and fermentation conditions when the engineered bacteria are configured as a production strain to produce keratinase to obtain a fermentation medium capable of increasing a yield of keratinase and an optimum process for fermentation production of keratinase.

The disclosure provides a recombinant *B. subtilis* engineered bacterium capable of efficiently expressing keratinase, wherein the engineered bacterium comprises a recombinant plasmid and an expression host, the recombinant plasmid comprises a target gene and an expression vector, the target gene is a keratinase gene (ker), the expression vector is pP43NMK, and the expression host is *B. subtilis*.

In one embodiment of the disclosure, the keratinase gene (ker) comes from *B. licheniformis* (BBE11-1).

In one embodiment of the disclosure, the keratinase gene (ker) has a nucleotide sequence of SEQ ID NO.1.

In one embodiment of the disclosure, the recombinant plasmid is obtained through amplifying a keratinase gene (ker) by specific primers with nucleotide sequences of SEQ ID NO.2 and SEQ ID NO.3 to obtain the amplified keratinase gene (ker), amplifying a pP43NMK vector by specific primers with nucleotide sequences of SEQ ID NO.4 and SEQ ID NO.5 to obtain the amplified linearized pP43NMK vector, and then performing homologous recombination on the amplified keratinase gene (ker) and the amplified linearized pP43NMK vector.

In one embodiment of the disclosure, the homologous recombination is performed with a homologous recombination kit.

In one embodiment of the disclosure, the expression host is *B. subtilis* WB600.

The disclosure provides a fermentation medium for producing keratinase, wherein the medium comprises 15-25 g/L peptone, 5-15 g/L yeast powder, 15-25 g/L sucrose, 2-4 g/L $KH_2PO_4$, 5-7 g/L $Na_2HPO_4$ and 0.2-0.4 g/L $MgSO_4$, and the medium has a pH of 6.0-8.0.

In one embodiment of the disclosure, the medium comprises 20 g/L peptone, 10 g/L yeast powder, 20 g/L sucrose, 3 g/L $KH_2PO_4$, 6 g/L $Na_2HPO_4$ and 0.3 g/L $MgSO_4$, and the medium has a pH of 7.0.

The disclosure provides a method for producing keratinase, wherein the method uses the above recombinant *B. subtilis* engineered bacterium capable of efficiently expressing keratinase and the above fermentation medium for producing keratinase.

In one embodiment of the disclosure, the method is to inoculate the above recombinant *B. subtilis* engineered bacterium capable of efficiently expressing keratinase into the above fermentation medium for producing keratinase, control a temperature, a pH and a dissolved oxygen, and feed glucose at a constant rate flow for fermentation.

In one embodiment of the disclosure, the method is to inoculate the above recombinant *B. subtilis* engineered bacterium capable of efficiently expressing keratinase into the above fermentation medium for producing keratinase at an inoculum size of 4-6%, control a temperature at 35-39° C., a pH at 6.0-8.0 and a dissolved oxygen at 25-35%, and feed glucose at a constant rate flow of 35-45 g/L/h for fermentation for 26-30 h.

The dissolved oxygen of the fermentation medium not inoculated with a bacterium solution of the recombinant *B. subtilis* engineered bacterium is 100%.

In one embodiment of the disclosure, the method is to inoculate the above recombinant *B. subtilis* engineered bacterium capable of efficiently expressing keratinase into the above fermentation medium for producing keratinase at an inoculum size of 5%, control a temperature at 37° C., a pH at 7.0 and a dissolved oxygen at 30%, and feed glucose at a constant rate flow of 40 g/L/h for fermentation for 28 h.

The disclosure provides application of the above recombinant *B. subtilis* engineered bacterium capable of efficiently expressing keratinase or the above fermentation medium for producing keratinase or the above method for producing keratinase to preparing keratinase, degrading keratin, preparing feed additives, preparing organic fertilizers and preparing detergents.

The disclosure successfully constructs a genetically engineered bacterium B. subtilis WB600-pP43NMK-ker capable of efficiently expressing keratinase by using a keratinase gene from B. licheniformis (BBE11-1) as a target gene, pP43NMK as an expression vector and B. subtilis WB600 as an expression host, and performs fermentation with the engineered bacterium, thereby making an enzyme activity in fermentation supernate up to 3329.3 U/mL.

The disclosure conducts in-depth research on fermentation media and fermentation conditions when the engineered bacteria are configured as a production strain to produce keratinase to obtain a fermentation medium capable of increasing a yield of keratinase and an optimum process for fermentation production of keratinase, and performs fermentation with the fermentation medium and the fermentation conditions in cooperation with the B. subtilis engineered bacteria of the disclosure, thereby making an enzyme activity in fermentation supernate up to 31015.6 U/mL.

DETAILED DESCRIPTION

Following examples are applied to non-restrictive interpretation of the technical scheme of the disclosure.

Media involved in following examples include:

seed medium: 5 g/L yeast powder, 10 g/L peptone and 5 g/L NaCl;

initial medium: 20 g/L peptone, 10 g/L yeast powder, 10 g/L glucose, 3 g/L $KH_2PO_4$, 6 g/L $Na_2HPO_4$ and 0.3 g/L $MgSO_4$; and optimized medium: 20 g/L peptone, 10 g/L yeast powder, 20 g/L sucrose, 3 g/L $KH_2PO_4$, 6 g/L $Na_2HPO_4$ and 0.3 g/L $MgSO_4$.

Detection method involved in following examples includes:

measurement of activity of keratinase: taking 50 μL of fermentation supernate that is properly diluted, and adding 150 μL of a 50 mM Gly/NaOH solution as a buffer solution and 100 μL of water-soluble keratin (purchased from TCI (Shanghai) Chemical Industry Development Co., Ltd., product code: K0043) with a concentration of 2.5% as a substrate to be evenly mixed for reaction for 20 min at 40° C.; adding 200 μL of 4% (w/v) trichloroacetic acid (TCA) to terminate the reaction for centrifuging at 8000 r/min for 3 min at room temperature; and taking 200 μL of supernatant, adding 1 mL of 4% (w/v) $Na_2CO_3$ and 200 μL of a Folin-phenol reagent to be evenly mixed for developing for 10 min at 50° C., and measuring a light absorption value of the supernate at 660 nm with a 0.5 cm quartz cell. 3 parallel examples are set for an experimental group, and blank control has same operations except for adding a reaction terminator TCA before adding the substrate.

One enzyme activity unit is defined as conversion of a keratin substrate every minute at 40° C. to release 1 μmol of tyrosine.

Figure 1:
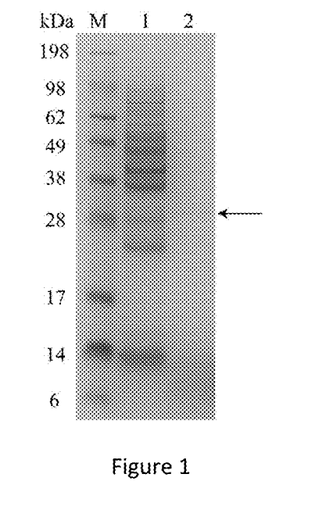
FIG. 1 shows an SDS-PAGE analysis result of fermentation supernate of a recombinant bacterium for expressing keratinase with different expression vectors, wherein 1 is B. subtilis WB600 fermentation liquor supernatant, and 2 is B. subtilis WB600-pP43NMK-ker fermentation liquor supernatant.
Figure 2:
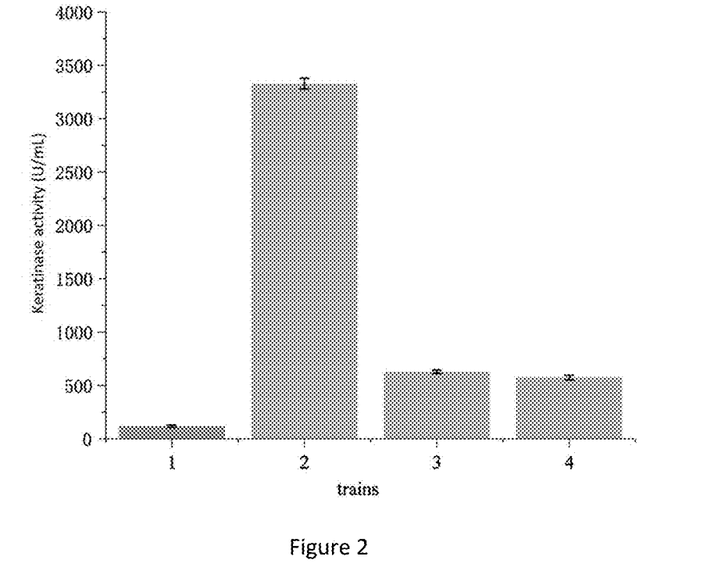
FIG. 2 shows an enzyme activity of fermentation supernate of a recombinant bacterium for expressing keratinase with different expression vectors, where 1 is wild keratinase, 2 is B. subtilis WB600-pP43NMK-ker, 3 is B. subtilis WB600-pMA5-ker, and 4 is B. subtilis WB600-pSTOP1622-ker.

Example 1: Construction of Keratinase Expressing Engineered Strain with Strong Promoter Specific constructions steps as follows:

(1) designing specific primers P1 and P2 (shown in Table 1) to amplify a wild B. licheniformis genome to obtain a keratinase gene ker under PCR amplification conditions of predegeneration for 30 min at 98° C., degeneration for 30 s at 98° C., annealing for 10 s at 55° C. and extension for 90 s at 72° C. (34 cycles);

(2) designing specific primers P3 and P4 (shown in Table 1) for amplification with a pP43NMK vector as a template to obtain linearized pP43NMK under PCR amplification conditions of predegeneration for 30 min at 98° C., degeneration for 30 s at 98° C., annealing for 10 s at 55° C. and extension for 7 min at 72° C. (25 cycles);

(3) designing specific primers P5 and P6 (shown in Table 1) for amplification with a pMA5 vector as a template to obtain linearized pMA5 under PCR amplification conditions of predegeneration for 30 min at 98° C., degeneration for 30 s at 98° C., annealing for 10 s at 55° C. and extension for 7 min 30 s at 72° C. (25 cycles);

(4) designing specific primers P7 and P8 (shown in Table 1) for amplification with a pSTOP1622 vector as a template to obtain linearized pSTOP1622 under PCR amplification conditions of predegeneration for 30 min at 98° C., degeneration for 30 s at 98° C., annealing for 10 s at 55° C. and extension for 6 min 30 s at 72° C. (25 cycles);

(5) quantifying purified genes and vector fragments with a nucleic acid quantitative analyzer NanoDrop 2000, obtaining recombinant plasmids pP43NMK-ker, pMA5-ker and pSTOP1622-ker with the homologous recombination kit (Clonexpress II One Step Cloning Kit), converting the obtained recombinant products into E. coli JM109, and enriching obtained positive clone and extracting a plasmid on a next day;

(6) converting the recombinant plasmids pP43NMK-ker, pMA5-ker and pSTOP1622-ker into B. subtilis WB600, and picking the positive clone to successfully construct genetically engineered strains B. subtilis WB600-pP43NMK-ker, B. subtilis WB600-pMA5-ker and B. subtilis WB600-pSTOP1622-ker for efficiently expressing keratinase;

(7) picking the positive clone to be cultured overnight in a seed medium to obtain a seed solution, and inoculating the seed solution into an initial medium at an inoculum size of 5% to be cultured for 28 h at 37° C. and 220 rpm;

(8) centrifuging fermentation liquor at 4° C. and 12000 rpm to obtain supernatant, detecting expression of keratinase with SDS-PAGE (detection results are shown in FIG. 1), and meanwhile measuring activities of keratinase in fermentation liquor supernatant (detection results are shown in FIG. 2); and (9) culturing B. licheniformis (BBE11-1) in a chicken feather medium for 48 h and then performing centrifuging, and detecting activities of keratinase in fermentation liquor supernatant of the B. licheniformis (BBE11-1).

Detection results of enzyme activities as follows: an enzyme activity of keratinase in fermentation supernate of the B. subtilis WB600-pP43NMK-ker is 3329.3 U/mL, an enzyme activity of keratinase in fermentation supernate of the B. subtilis WB600-pMA5-ker is 628.6 U/mL, and an enzyme activity of keratinase in fermentation supernate of the B. subtilis WB600-pSTOP1622-ker is 574.1 U/mL, which are 27.7 times, 5.2 times and 4.8 times that of wild keratinase (120 U/mL) respectively.

TABLE 1

Primers

| Name | Sequence |
|---|---|
| P1 | SEQ ID NO. 2:<br>GGTAAGAGAGGAATGTACACATGATGAGGAAAAAGAGTTTTTGGC |
| P2 | SEQ ID NO. 3:<br>ATTACGCCAAGCTTTCATCATTATTGAGCGGCAGCTTCG |
| P3 | SEQ ID NO. 4:<br>TGATGAAAGCTTGGCGTAATCATGGTCATAGCTG |
| P4 | SEQ ID NO. 5:<br>GTGTACATTCCTCTCTTACCTATAATGGTACCGCTATCACT |
| P5 | SEQ ID NO. 6:<br>GGAATTCCATATGAGGAAAAAGAGTTTTTGG |
| P6 | SEQ ID NO. 7:<br>CGCGGATCCTTATTGAGCGGCAGCTTCG |
| P7 | SEQ ID NO. 8:<br>TCCAAACTAGTTCGAAGATCTATGATGAGGAAAAAGAGTTTTTGGC |
| P8 | SEQ ID NO. 9:<br>CATGCGGCCGGTACCGGATCCTTATTGAGCGGCAGCTTCG |

Figure 3:
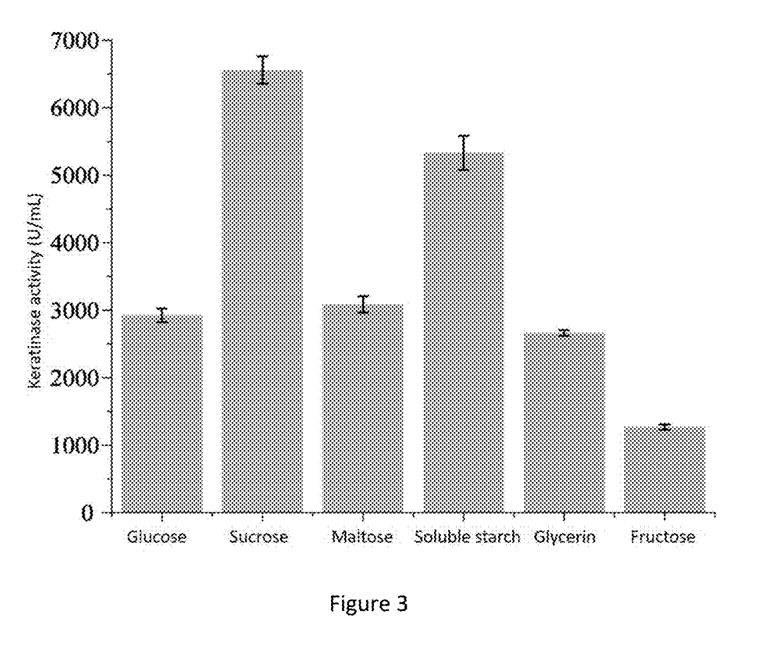
FIG. 3 shows enzyme activities of fermentation supernate of a recombinant bacterium cultured with different carbon sources.

Example 2: Influences of Carbon Sources on Yield of Keratinase (1) 6 types of 20 g/L carbon sources (glucose, sucrose, maltose, soluble starch, glycerin and fructose) were selected and, together with 20 g/L peptone, 10 g/L yeast powder, 3 g/L $KH_2PO_4$, 6 g/L $Na_2HPO_4$ and 0.3 g/L $MgSO_4$, were configured into an initial medium for single-factor experiments; and (2) the engineered bacterium B. subtilis WB600-pP43NMK-ker obtained in Example 1 was inoculated into the initial medium to be cultured for 28 h at 37° C. and 220 rpm, and activities of keratinase in fermentation liquor supernatant were measured (detection results are shown in FIG. 3).

Detection results of enzyme activities: an enzyme activity of keratinase in supernate obtained by using glucose for recombinant bacterium fermentation is 2922.4 U/mL, an enzyme activity of keratinase in supernate obtained by using sucrose for recombinant bacterium fermentation is 6557.5 U/mL, an enzyme activity of keratinase in supernate obtained by using maltose for recombinant bacterium fermentation is 3085.6 U/mL, an enzyme activity of keratinase in supernate obtained by using soluble starch for recombinant bacterium fermentation is 5330.2 U/mL, an enzyme activity of keratinase in supernate obtained by using glycerin for recombinant bacterium fermentation is 2662.7 U/mL, and an enzyme activity of keratinase in supernate obtained by using fructose for recombinant bacterium fermentation is 1266.5 U/mL, which indicates that the sucrose is the optimal carbon source.

Figure 4:
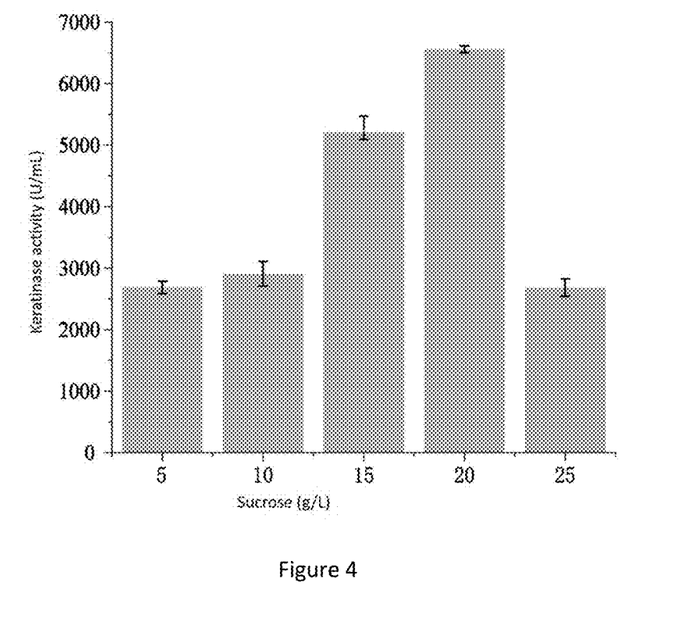
FIG. 4 shows enzyme activities of fermentation supernate of a recombinant bacterium cultured with sucrose of different concentrations.

Example 3: Influences of Concentrations of Carbon Sources on Yield of Keratinase (1) 5 types of sucrose of different concentrations (5 g/L, 10 g/L, 15 g/L, 20 g/L and 25 g/L) were selected and, together with 20 g/L peptone, 10 g/L yeast powder, 3 g/L $KH_2PO_4$, 6 g/L $Na_2HPO_4$ and 0.3 g/L $MgSO_4$, were configured into an initial medium for single-factor experiments; and (2) the engineered bacterium B. subtilis WB600-pP43NMK-ker obtained in Example 1 was inoculated into the initial medium to be cultured for 28 h at 37° C. and 220 rpm, and activities of keratinase in fermentation liquor supernatant were measured (detection results are shown in FIG. 4).

Detection results of enzyme activities: an enzyme activity of keratinase in supernate obtained by using 5 g/L sucrose for recombinant bacterium fermentation is 2687.3 U/mL, an enzyme activity of keratinase in supernate obtained by using 10 g/L sucrose for recombinant bacterium fermentation is 2909.1 U/mL, an enzyme activity of keratinase in supernate obtained by using 15 g/L sucrose for recombinant bacterium fermentation is 5212.0 U/mL, an enzyme activity of keratinase in supernate obtained by using 20 g/L sucrose for recombinant bacterium fermentation is 6557.5 U/mL, and an enzyme activity of keratinase in supernate obtained by using 25 g/L sucrose for recombinant bacterium fermentation is 2682.3 U/mL, which indicates that the optimal concentration of the sucrose is 20 g/L.

Figure 5:
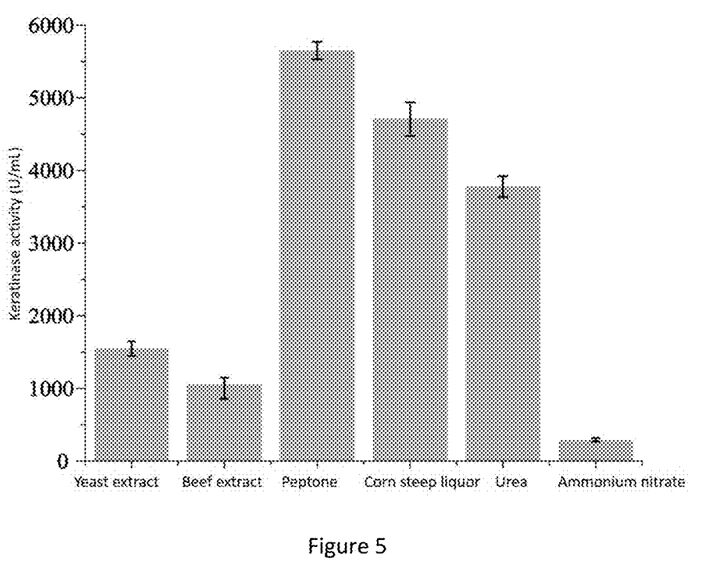
FIG. 5 shows enzyme activities of fermentation supernate of a recombinant bacterium cultured with different nitrogen sources.

Example 4: Influences of Nitrogen Sources on Yield of Keratinase (1) 6 types of 20 g/L nitrogen sources (yeast extract, beef extract, peptone, corn steep liquor, urea and ammonium nitrate) were selected and, together with 20 g/L sucrose, 10 g/L yeast powder, 3 g/L $KH_2PO_4$, 6 g/L $Na_2HPO_4$ and 0.3 g/L $MgSO_4$, were configured into an initial medium for single-factor experiments; and (2) the engineered bacterium B. subtilis WB600-pP43NMK-ker obtained in Example 1 was inoculated into the initial medium to be cultured for 28 h at 37° C. and 220 rpm, and activities of keratinase in fermentation liquor supernatant were measured (detection results are shown in FIG. 5).

Detection results of enzyme activities: an enzyme activity of keratinase in supernate obtained by using a yeast extract for recombinant bacterium fermentation is 1549.1 U/mL, an enzyme activity of keratinase in supernate obtained by using a beef extract for recombinant bacterium fermentation is 1056.2 U/mL, an enzyme activity of keratinase in supernate obtained by using peptone for recombinant bacterium fermentation is 5651.9 U/mL, an enzyme activity of keratinase in supernate obtained by using corn steep liquor for recombinant bacterium fermentation is 4714.3 U/mL, an enzyme activity of keratinase in supernate obtained by using urea for recombinant bacterium fermentation is 3778.3 U/mL, and an enzyme activity of keratinase in supernate obtained by using ammonium nitrate for recombinant bacterium fermentation is 293.6 U/mL, which indicates that the peptone is the optimal nitrogen source.

Figure 6:
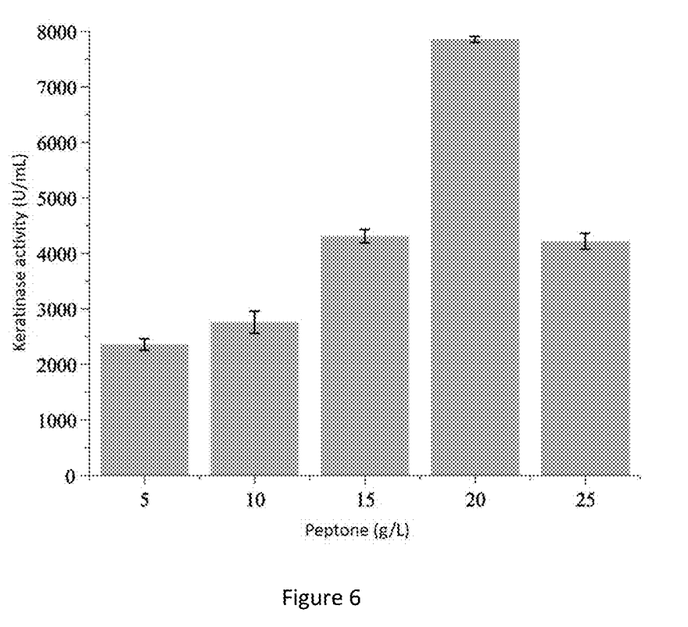
FIG. 6 shows enzyme activities of fermentation supernate of a recombinant bacterium cultured with peptone of different concentrations.

Example 5: Influences of Concentrations of Nitrogen Source on Yield of Keratinase (1) 5 types of peptone of different concentrations (5 g/L, 10 g/L, 15 g/L, 20 g/L and 25 g/L) were selected and, together with 20 g/L sucrose, 10 g/L yeast powder, 3 g/L $KH_2PO_4$, 6 g/L $Na_2HPO_4$ and 0.3 g/L $MgSO_4$, were configured into an initial medium for single-factor experiments; and (2) the engineered bacterium *B. subtilis* WB600-pP43NMK-ker obtained in Example 1 was inoculated into the initial medium to be cultured for 28 h at 37° C. and 220 rpm, and activities of keratinase in fermentation liquor supernatant were measured (detection results are shown in FIG. 6).

Detection results of enzyme activities: an enzyme activity of keratinase in supernate obtained by using 5 g/L peptone for recombinant bacterium fermentation is 2360.6 U/mL, an enzyme activity of keratinase in supernate obtained by using 10 g/L peptone for recombinant bacterium fermentation is 2758.1 U/mL, an enzyme activity of keratinase in supernate obtained by using 15 g/L peptone for recombinant bacterium fermentation is 4307.6 U/mL, an enzyme activity of keratinase in supernate obtained by using 20 g/L peptone for recombinant bacterium fermentation is 7856.7 U/mL, and an enzyme activity of keratinase in supernate obtained by using 25 g/L peptone for recombinant bacterium fermentation is 4217.3 U/mL, which indicates that the optimal concentration of the peptone is 20 g/L.

In conclusion of Examples 2-5, the optimized medium which contains 20 g/L peptone, 10 g/L yeast powder, 20 g/L sucrose, 3 g/L $KH_2PO_4$, 6 g/L $Na_2HPO_4$ and 0.3 g/L $MgSO_4$ and has a pH of 7.0 is obtained.

The genetically engineered strain *B. subtilis* WB600-pP43NMK-ker undergoes fermentation production keratinase verification with the optimized medium, and after the genetically engineered strain is cultured for 28 h at 37° C. and 220 rpm, the activity of keratinase in fermentation supernate reaches 7856.7 U/mL, which is 2.4 times that of the initial medium and 65.5 times that of the wild keratinase.

Figure 7:
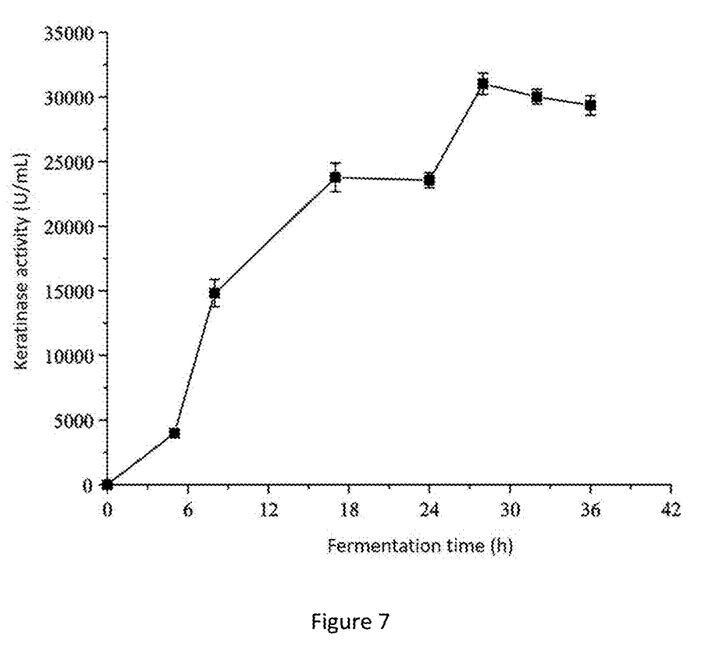
FIG. 7 shows an enzyme activity tendency of fermentation supernate of a recombinant bacterium fermented with a 3-L fermentation tank system.

Example 6: Genetically Engineered Bacteria Supplemented in Batches and Cultured by 3 L Fermentation Tank for Efficiently Producing Keratinase A fermentation process of *B. subtilis* WB600-pP43NMK-ker in the 3 L fermentation tank was controlled and optimized, and specific fermentation steps are as follows:

(1) inoculating glycerin bacteria of the *B. subtilis* WB600-pP43NMK-ker into a seed medium at a ratio of 1/1000 to be cultured for 12 h at 37° C. and 220 rpm to obtain a first-stage seed solution, and transferring the first-stage seed solution into a seed medium at a ratio of 1/100 to be cultured for 4 h at 37° C. and 220 rpm to obtain a second-stage seed solution;

(2) adding 1.5 L of the optimized medium obtained in Examples 2-5 into the 3 L fermentation tank to be processed for 20 min at 121° C. and then cooled to room temperature, adjusting an initial pH to 7.0, a temperature to 37° C., a rotating speed to 600 rpm and a ventilatory volume to 2.0 vvm, and inoculating the second-stage seed solution according to an inoculum size of 5%;

(3) providing bacterium growth demands for 6 h by initial sucrose, since the initial sucrose is used up at the $6^{th}$ h, feeding glucose at a constant rate flow of 28.8 g/L·$h^{-1}$ between $6^{th}$ h-$18^{th}$ h, and stopping low feeding at the 18th h until fermentation ends;

(4) performing a real-time pH adjustment for the fermentation process with ammonia water and phosphoric acid, controlling a pH at about 7.0 and a temperature of the fermentation process at 37° C., and controlling a system dissolved oxygen at about 30% by adjusting a stirring rotating speed and a ventilatory volume in the fermentation process; and (5) performing sampling for the fermentation process, centrifuging fermentation liquor at 4° C. and 12000 rpm to obtain supernatant, and measuring the highest activity of keratinase in the fermentation supernate at 31015.6 U/mL at the 28th h of fermentation, which is 258 times of the activity (120 U/mL) of the wild keratinase (detection results are shown in FIG. 7).

What is claimed is:

1. A method of producing keratinase, which comprises:
culturing a recombinant engineered bacterium in a fermentation medium for 26 to 30 hours;
wherein the recombinant engineered bacterium comprises a recombinant plasmid,
wherein the recombinant plasmid comprises a target gene and an expression vector,
wherein the target gene is a keratinase gene (ker) comprising nucleotide sequence SEQ ID NO:1,
wherein the expression vector is pP43NMK,
wherein the expression host is *Bacillus subtilis*,
wherein the fermentation medium comprises:
15 g/L to 25 g/L peptone,
5 g/L to 15 g/L yeast powder,
15 g/L to 25 g/L sucrose,
2 g/L to 4 g/L $KH_2PO_4$,
5 g/L to 7 g/L 5-7 g/L $Na_2HPO_4$, and
0.2 g/L to 0.4 g/L $MgSO_4$,
wherein the medium has a pH of 6.0 to 8.0, and
wherein the keratinase produced thereby possesses an enzyme activity of at least 3329.2 U/mL to 6557.5 U/mL, or at least 27.7 times higher than wild type keratinase activity (120 U/mL).

2. The method of claim 1, further comprising:
inoculating the recombinant engineered bacterium into the fermentation medium,
controlling temperature, pH, and dissolved oxygen, and feeding glucose at a constant rate.

3. The method of claim 1, wherein the culturing the recombinant engineered bacterium comprises:
inoculating the recombinant engineered bacterium into the fermentation medium,
controlling a temperature at 35° C. to 39° C., a pH at 6.0 to 8.0, and a dissolved oxygen at 25% to 35%, and
feeding glucose at a constant rate flow of 35 g/L/h to 45 g/L/h.

4. The method of claim 1, wherein the culturing the recombinant engineered bacterium comprises:
inoculating the recombinant engineered bacterium into the fermentation at an inoculum size of 5%,
controlling a temperature at 37° C., a pH at 7.0, and a dissolved oxygen at 30%, and
feeding glucose at a constant rate flow of 40 g/L/h for 28 hours.

* * * * *

SEQUENCE LISTING

<160> NUMBER OF SEQ ID NOS: 9

<210> SEQ ID NO 1
<211> LENGTH: 1140
<212> TYPE: DNA
<213> ORGANISM: Artificial sequence
<220> FEATURE:
<223> OTHER INFORMATION: Synthetic DNA

<400> SEQUENCE: 1

```
atgatgagga aaaagagttt ttggcttggg atgctgacgg ccttaatgct cgtgttcacg      60
atggccttca gcgattccgc gtctgctgct cagccggcga aaaatgttga aaaggattat     120
attgtcggat ttaagtcagg agtgaaaacc gcatccgtca aaaggacat catcaaagag      180 agcggcggaa aagtggacaa gcagtttaga atcatcaacg cggcaaaagc gaagctagac    240
aaagaagcgc ttaaggaagt caaaaatgat ccggatgtcg cttatgtgga agaggatcat    300
gtggcccatg ccttggcgca aaccgttcct tacggcattc ctctcattaa agcggacaaa    360
```

```
gtgcaggctc aaggctttaa gggagcgaat gtaaaagtag ccgtcctgga tacaggaatc    420
caagcttctc atccggactt gaacgtagtc ggcggagcaa gctttgtggc tggcgaagct    480
tataacaccg acggcaacgg acacggcaca catgttgccg gtacagtagc tgcgcttgac    540
aatacaacgg gtgtattagg cgttgcgcca agcgtatcct tgtacgcggt taaagtactg    600
aattcaagcg gaagcggatc atacagcggc attgtaagcg gaatcgagtg ggcgacaaca    660
aacggcatgg atgttatcaa tatgagcctt gggggagcat caggctcgac agcgatgaaa    720
caggcagtcg acaatgcata tgcaagaggg gttgtcgttg tagctgcagc agggaacagc    780
ggatcttcag gaaacacgaa tacaattggc tatcctgcga aatacgattc tgtcatcgct    840
gttggtgcgg tagactctaa cagcaacaga gcttcatttt ccagtgtggg agcagagctt    900
gaagtcatgg ctcctggcgc aggcgtatac agcacttacc caacgaacac ttatgcaaca    960
ttgaacggaa cgtcaatggc ttctcctcat gtagcgggag cagcagcttt gatcttgtca   1020
aaacatccga acctttcagc ttcacaagtc cgcaaccgtc tctccagcac ggcgacttat   1080
ttgggaagct ccttctacta tgggaaaggt ctgatcaatg tcgaagctgc cgctcaataa   1140

<210> SEQ ID NO 2
<211> LENGTH: 45
<212> TYPE: DNA
<213> ORGANISM: Artificial sequence
<220> FEATURE:
<223> OTHER INFORMATION: Synthetic DNA

<400> SEQUENCE: 2
ggtaagagag gaatgtacac atgatgagga aaaagagttt ttggc                      45

<210> SEQ ID NO 3
<211> LENGTH: 39
<212> TYPE: DNA
<213> ORGANISM: Artificial sequence
<220> FEATURE:
<223> OTHER INFORMATION: Synthetic DNA

<400> SEQUENCE: 3
attacgccaa gctttcatca ttattgagcg gcagcttcg                             39

<210> SEQ ID NO 4
<211> LENGTH: 34
<212> TYPE: DNA
<213> ORGANISM: Artificial sequence
<220> FEATURE:
<223> OTHER INFORMATION: Synthetic DNA

<400> SEQUENCE: 4
tgatgaaagc ttggcgtaat catggtcata gctg                                  34

<210> SEQ ID NO 5
<211> LENGTH: 41
<212> TYPE: DNA
<213> ORGANISM: Artificial sequence
<220> FEATURE:
<223> OTHER INFORMATION: Synthetic DNA

<400> SEQUENCE: 5
gtgtacattc ctctcttacc tataatggta ccgctatcac t                          41

<210> SEQ ID NO 6
<211> LENGTH: 31
<212> TYPE: DNA
```

```
<213> ORGANISM: Artificial sequence
<220> FEATURE:
<223> OTHER INFORMATION: Synthetic DNA

<400> SEQUENCE: 6
ggaattccat atgaggaaaa agagtttttg g                            31

<210> SEQ ID NO 7
<211> LENGTH: 28
<212> TYPE: DNA
<213> ORGANISM: Artificial sequence
<220> FEATURE:
<223> OTHER INFORMATION: Synthetic DNA

<400> SEQUENCE: 7
cgcggatcct tattgagcgg cagcttcg                                28

<210> SEQ ID NO 8
<211> LENGTH: 46
<212> TYPE: DNA
<213> ORGANISM: Artificial sequence
<220> FEATURE:
<223> OTHER INFORMATION: Synthetic DNA

<400> SEQUENCE: 8
tccaaactag ttcgaagatc tatgatgagg aaaaagagtt tttggc            46

<210> SEQ ID NO 9
<211> LENGTH: 40
<212> TYPE: DNA
<213> ORGANISM: Artificial sequence
<220> FEATURE:
<223> OTHER INFORMATION: Synthetic DNA

<400> SEQUENCE: 9
catgcggccg gtaccggatc cttattgagc ggcagcttcg                   40
```